United States Patent [19]

Hato et al.

[11] Patent Number: 4,619,897

[45] Date of Patent: Oct. 28, 1986

[54] ENZYME IMMOBILIZATION IN A FLUORINE RESIN MEMBRANE

[75] Inventors: Masakatsu Hato; Yukio Shimura; Keishiro Tsuda, all of Ibaraki, Japan

[73] Assignees: Agency of Industrial Science & Technology; Ministry of International Trade & Industry, both of Tokyo, Japan

[21] Appl. No.: 540,618

[22] Filed: Oct. 11, 1983

[30] Foreign Application Priority Data

Oct. 12, 1982 [JP] Japan ................... 57-178669

[51] Int. Cl.⁴ ............ C12N 11/04; C12N 11/08; C12N 11/02; C12N 11/00
[52] U.S. Cl. ..................... 435/182; 435/180; 435/177; 435/174
[58] Field of Search .............. 435/182, 180, 177, 174

[56] References Cited

U.S. PATENT DOCUMENTS

| | | | |
|---|---|---|---|
| 3,843,443 | 10/1974 | Fishman | 435/181 |
| 4,240,889 | 12/1980 | Yoda et al. | 435/180 |
| 4,251,631 | 2/1981 | Simon et al. | 435/180 |
| 4,317,879 | 3/1982 | Busby et al. | 435/182 |
| 4,323,650 | 4/1982 | Rosevear | 435/182 |
| 4,464,468 | 8/1984 | Avrameas et al. | 435/182 |

OTHER PUBLICATIONS

Mascini, M. and Guilbault, G. G., "Urease Coupled Ammonia Electrode for Urea Determination in Blood Serum," Anal. Chem., vol. 49, No. 6, May 1977, pp. 795–798.

*Primary Examiner*—David M. Naff
*Assistant Examiner*—L. Krawczewicz
*Attorney, Agent, or Firm*—Oblon, Fisher, Spivak, McClelland & Maier

[57] ABSTRACT

A fluorine resin membrane is made hydrophilic to a prescribed depth in the direction of thickness thereof to produce an asymmetrical membrane having a hydrophilic portion and a hydrophobic portion. An enzyme is immobilized in the hydrophilic portion of the membrane to obtain a membrane having a function of enzymatic reaction and a function of selective gas permeation. The hydrophilic portion is formed by causing a perfluoroalkyl surface active agent to penetrate the prescribed depth that is to be hydrophilic.

9 Claims, 2 Drawing Figures

ENZYME IMMOBILIZATION IN A FLUORINE RESIN MEMBRANE

BACKGROUND OF THE INVENTION

This invention relates to a novel asymmetrically functional membrane possessing an asymmetrical stratal structure and combining a function of selective gas permeation and a function of enzymatic reaction and to a method for the manufacture thereof. More particularly, this invention relates to an asymmetrical porous fluorine type resin membrane of a structure consisting of a hydrophilic layer and a hydrophobic layer, to an asymmetrically functional membrane obtained by immobilizing an enzyme in the hydrophilic layer of said asymmetrical membrane thereby imparting said membrane with both a function of enzymatic reaction and a function of selective permeation of gas, and to a method for the manufacture thereof.

The background of this invention will now be outlined in the following.

Enzyme-immobilized membranes are useful as sensing elements for enzyme electrodes, for example. For these membranes to give reliable response and produce consistent results, they must be manufactured in constant activity, thickness and configuration. Moreover, the membranes must be capable of high-speed response in order to permit rapid analysis and must have sufficient mechanical strength to provide stable continuous operation over prolonged periods.

An enzyme electrode consists of an enzyme-immobilized membrane and an electrochemical device. Typical electrochemical devices commonly used in the enzyme electrode are such selective electrodes as the ammonia gas selective electrode, the carbon dioxide gas selective electrode and the oxygen selective electrode. Basically, an enzyme electrode using these electrochemical devices needs at least two separate membranes of contrasting properties, i.e., a hydrophobic gas permeable membrane (usually a porous polytetrafluoroethylene membrane) on one hand, and an enzyme immobilized hydrophilic membrane on the other hand. The need for the employment of two membranes leads to various drawbacks with respect to response time, simplicity of electrode construction and long-term stability. It is clear that sufficiently close contact of the two membranes on a sensing end of an electrochemical device is prerequisite for a rapid electrode response. However, with two membranes, it is rather tedious and time consuming to construct the electrode in such a manner as the two membranes and the electrochemical devices come into close contact with each other, e.g., small air bubbles are often trapped between the two membranes and/or the membrane and the electrochemical device, leading to a sluggish electrode response. Moreover, the contact tends to loosen with time, due to differences in their mechanical properties. This results in a gradual slow down of the response time, and replacement of the enzyme membrane with another one is needed even if the enzyme activity remains unaffected.

These drawbacks may be avoided by direct formation of an enzyme membrane over a gas permeable membrane. For example, Mascini (M. Mascini. et al., Anal. Chem., 49, 795 (1977)) and Anfält (T. Anfält, et al., Anal Lett., 1973, 969) separately tried direct formation of an enzyme membrane on a porous membrane of polytetrafluoroethylene. The composite membrane obtained in this case is not practical because the enzyme membrane and the polytetrafluoroethylene resin adhere to each other with extremely weak strength and they readily separate from each other during use. Schultze (Schultze et al., Trans. Am. Soc. Artif, Intern. Organs XXV, p 66 (1979)) treated the surface of polytetrafluoroethylene membrane with an etching solution consisting of metallic sodium and an organic solvent then directly formed a gel membrane of glucose oxidase-albumin on the treated surface. Although this method enables the polytetrafluoroethylene membrane and the enzyme membrane to adhere to each other with greater strength than the method described above, the composite membrane obtained by this method is unstable and unsuitable for practical application since separation of the membranes cannot be prevented because the enzyme membrane of low mechanical strength is simply superposed on the surface of the polytetrafluoroethylene membrane without any protection. Further by this method, it is difficult to reproducibly obtain an enzyme membrane of fixed thickness at all times. Moreover, since the treatment with the etching solution alters the polytetrafluoroethylene membrane configuration, it is difficult to obtain treated membranes having constant response characteristics. Therefore, the produced composite membrane is not suitable for use in a sensor which is particularly required to maintain constant response characteristics even when the composite membrane is replaced with a new one.

As a membrane superior to those obtained by the above described methods, there has been developed an asymmetrically functional membrane which is produced by immobilizing an enzyme within continuous micropores distributed to a fixed depth d in the direction of thickness in a porous fluorine type resin membrane of a thickness of D (d<D) thereby enabling the layer of thickness d of the membrane to serve as an enzyme-immobilized membrane having a function of enzymatic reaction and the remaining layer of thickness D−d of the membrane to serve as a membrane having a function of selective gas permeation. Even if, in this case, the enzyme membrane is in the form of mechanically weak gel, it acquires amply high mechanical strength because it is embedded in the strong matrix of the fluorine type resin membrane and thus is protected by the matrix. This asymmetrical functional membrane is superior to the earlier developed membranes produced by joining separately produced enzyme-immobilized and fluorine type gas permeable membranes since it allows a membrane of the same function to be obtained by processing only a single membrane. In the production of such a membrane, however, it is necessary to cause an enzyme solution to permeate the continuous micropores of the fluorine type resin membrane in order to immobilize the enzyme in the membrane. However, since, the membrane being hydrophobic, it is extremely difficult to incorporate the enzyme solution into the micropores. For successful immobilization of the enzyme, therefore, the fluorine type resin membrane must be given a treatment for making the resin hydrophilic without changing micropore structure of the membrane.

Various methods have been available for making a fluorine type resin hydrophilic. These include, for example, treatment with a metallic sodium-organic solvent (or ammonia) system, graft reaction by the use of radiation, a method involving use of an organic titanium compound, adsorption treatment by the use of a surface active agent or a hydrophilic high molecular compound, plasma treatment, and corona-discharge treatment. When any of these known methods is applied to a porous fluorine type resin membrane having a thickness on the order of 20 to 100 μm, it is only possible to make the membrane hydrophilic throughout the entire thickness thereof or to make it hydrophilic only to a small depth from the treated surface. None of these conventional methods has been able to provide a sophisticated treatment enabling the membrane to be made hydrophilic only to a desired thickness without changing the original micropore structure. When the membrane is made hydrophilic throughout the entire thickness, it is deprived of its function of selective gas permeation and is no longer useful as an enzyme electrode. When the membrane is rendered hydrophilic only in its surface region, it is incapable of stably immobilizing an ample amount of enzyme for the membrane to produce sufficiently large output.

One object of this invention is to provide an asymmetrically functional membrane of fluorine type resin having a desired thickness thereof selectively made hydrophilic.

Another object of this invention is to provide an asymmetrically functional membrane of fluorine type resin which combines a function of enzymatic reaction and a function of selective gas permeation.

Yet another object of this invention is to provide a method for the manufacture of an asymmetrically functional membrane of fluorine type resin which combines a function of enzymatic reaction and a function of selective gas permeation.

SUMMARY OF THE INVENTION

The inventors conducted various studies with a view to attaining the objects described above. They have consequently learned that a membrane of porous fluorine type resin having a thickness on the order of 100 μm is made hydrophilic selectively to a desired depth in the direction of thickness by using a solution of fluorinated surface active agent which permeates the continuous micropores in the fluorine type resin at an accurately controllable speed. This invention has been perfected on the basis of this knowledge. In accordance with this invention, since the treatment for making the membrane hydrophilic utilizes a solution of fluorinated surface active agent of known permeating speed, the time required for this solution to permeate the micropores to a desired thickness d of the membrane is easily determined. When one side of a given porous fluorinated resin membrane is brought in contact with the solution of surface active agent for a fixed length of time and then quickly washed with water, therefore, the surface active agent is allowed to permeate the wetted side of the membrane to the prescribed thickness and to deposit on the surface of the continuous micropores within this thickness, making a layer of this thickness of the membrane hydrophilic. Consequently, there is obtained an asymmetrically functional membrane of fluorine type resin formed of the two layers, i.e. a hydrophilic layer of the thickness d and a hydrophobic layer of the remaining thickness D−d, and possessed of a function of selective gas permeation. The hydrophilic portion of the asymmetrically functional membrane obtained by the treatment described above permits easy permeation of an enzyme solution. When this portion is treated for immobilization of an enzyme, therefore, there is obtained a membrane combining a function of enzymatic reaction and a function of selective gas permeation. An enzyme electrode which is produced by superposing this asymmetrically functional membrane firmly on a sensing end of an electrode provides a stable output for a long time.

DESCRIPTION OF THE PREFERRED EMBODIMENTS

As the starting material for the product aimed at by the present invention a porous fluorine type resin membranes of any description may be utilized without reference to kind, method of manufacture, thickness, shape, or size. Preferable examples are an expanded polytetrafluoroethylene membrane having a thickness of 200 to 10 μm and an average pore diameter of 0.01 μm to 10 μm and a sintered porous polytetrafluoroethylene membrane produced by the finely divided particle sintering method. Particularly suitable for the purpose of this invention is an expanded polytetrafluoroethylene membrane or sintered polyetrafluoroethylene membrane having a thickness of 200 μm to 50 μm and a pore diameter of 0.1 μm to 1 μm.

The fluorinated surface active agent to be used for this invention is a surface active agent of the type having a fluorocarbon chain in the place of a hydrocarbon chain contained in the ordinary surface active agent. The chemical structure of this fluorinated surface active agent is not critical insofar as the surface active agent satisfies the condition that the aqueous solution thereof should possess surface tension of not more than 22 dynes/cm and exhibit an ability to be adsorbed on the fluorine type resin. Generally, a fluorinated surface active agent of an amphoteric or nonionic type proves to be advantageous over one of a cationic or anionic type because the former types possess a higher ability to lower surface tension and exerts a milder effect upon the enzyme than the latter. Preferable examples of the fluorinated surface active agent answering this description are perfluoroalkyl sulfonates, perfluoroalkyl carbonates, perfluoroalkyl phosphoric esters, perfluoroalkyl sulfates, perfluoroalkyl trimethylammonium salts, perfluoroalkyl betaines, and perfluoroalkyl ethylene oxide adducts. Particularly perfluoroalkyl betaines of amphoteric nature and perfluoroalkyl ethylene oxide adducts of nonionic nature are preferred choices.

In the present invention, the fluorinated surface active agent is generally used in the form of an aqueous solution. For the purpose of enhancing the solubility of the surface active agent, the fluorinated surface active agent may be used in the form of a mixed solvent incorporating a small amount of an organic solvent. Examples of organic solvents which are advantageously used for this purpose include lower alcohols such as ethanol and 2-propanol and ethers such as dioxane. Since excess addition of such an organic solvent results in a sharp rise in the speed of permeation of the surface active agent in the fluorine type resin possibly to the extent of making it difficult to control the depth of permeation, the concentration of organic solvent is generally not more than 10%.

Figure 1:
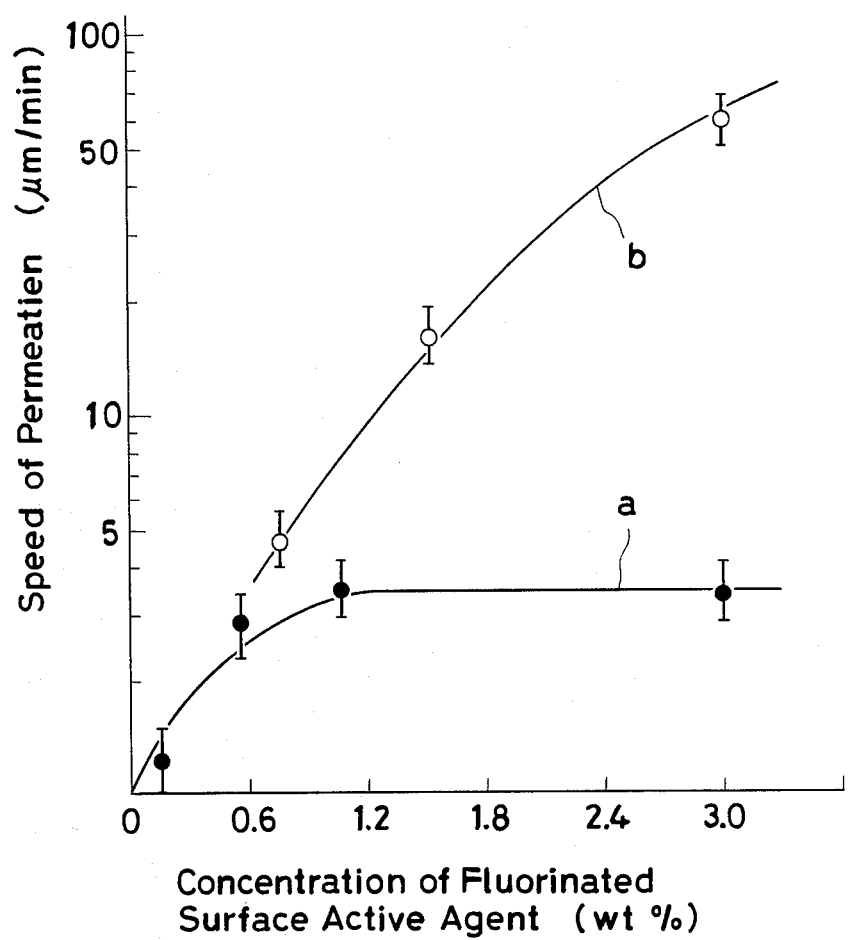
FIG. 1 is a graph showing the relation between the speed of permeation of a solution of fluorinated surface active agent into a porous fluorine type resin membrane and the concentration of the surface active agent.

For the present invention, accurate control of the speed of permeation of the surface active agent in the fluorine type resin is critical. When the speed of permeation is extremely high and the surface active agent permeates the entire depth of the memtrane in a matter of several seconds, for example, the desired accurate control of the depth of permeation cannot be realized and the ability of the membrane to provide selective gas permeation is lost. When the speed of permeation is extremely low, the treatment of the membrane requires an excessively long time. Although no optimum speed of permeation is specifically defined, any speed at which the permeation to a desired membrane depth is obtained by a treatment over a period of 5 to 20 minutes generally proves advantageous. When a porous fluorine type resin having a thickness of 100 $\mu$m is desired to be made hydrophilic on one side to a depth of 50 $\mu$m, for example, the treatment for conferring hydrophilicity to the depth of 50 $\mu$m may be completed within 5 to 10 minutes by selecting the speed of permeation in the range of 5 $\mu$m/min to 10 $\mu$m/min. Since the speed of permeation depends on numerous factors including the surface tension and viscosity of the surface active agent solution, the contact angle of the surface active agent solution relative to the fluorine type resin, the pore diameter of the membrane, and the shape and length of the pores, it is difficult to write a formula applicable to all conditions. It is, however, easy to determine empirically the speed of permeation. Thus, the speed of permeation in a given circumstance, therefore, may be predetermined by an experiment. FIG. 1 illustrates the relation between the speeds of permeation of (a) an amphoteric (perfluoroalkyl betaine) and (b) a nonionic (perfluoroalkyl ethylene oxide adduct) fluorine type surface active agent (determined in terms of the length of time required for the given solution to permeate a membrane from one surface to the other surface) and the concentration of surface active agent obtained of an expanded porous polytetrafluoroethylene membrane having a thickness of 70 $\mu$m and a pore diameter of 0.3 $\mu$m. From FIG. 1, it is noted that the amphoteric surface active agent used in a concentration of 1.0% permeates the membrane at a speed of 3.5 $\mu$m/min. To confer hydrophilicity upon one side of this membrane to a depth of 35 $\mu$m, i.e. to one half of the total thickness 70 $\mu$m of the membrane, therefore, the permeation treatment should be carried out for a period of 10 minutes.

By treating the membrane as described above, there is easily obtained an asymmetrically functional fluorine resin membrane of a stratal structure combining a hydrophilic layer and a hydrophobic layer. The thickness ratio of the hydrophilic layer and the hydrophobic layer thus formed in the membrane is required to fall in the range of from 8:2 to 3:7.

By further impregnating the resin membrane with an aqueous solution containing an enzyme and a gel forming agent thereby immobilizing the enzyme in the resin membrane, there is obtained an asymmetrically functional fluorine resin membrane which has an enzyme-containing gel substance filling up the micropores in the hydrophilic layer and combines a function of enzymatic reaction and a function of selective gas permeation.

The enzyme to be immobilized in the asymmetrically functional resin membrane of this invention is not specifically defined. Examples of the enzyme usable for this purpose include creatinase, nitrous acid reductase, L-amino acid oxidase, alcohol dehydrogenase, and glutamate dehydrogenase besides the enzymes indicated in the working examples cited herein below.

Now, the present invention will be described more specifically hereinbelow with reference to working examples. In the working examples there were used membranes made of polytetrafluoroethylene as a representative fluorine type resin. This particular fluorine type resin was adopted purely because it has the highest degree of hydrophobicity. The use of this particular fluorine type resin, therefore, is not meant to limit this invention with respect to the type of resin to be used.

EXAMPLE 1

On the surface of a circular membrane of expanded porous polytetrafluoroethylene 1.5 cm in diameter, 70 $\mu$m in thickness, 0.3 $\mu$m in average pore diameter, 0.709 in apparent density, and 60% in void ratio, a 1% aqueous solution of amphoteric fluorinated surface active agent (having perfluoroalkyl betaine as its principal component; made by Asahi Glass and marketed under trademark Surfron S-131) was dropped and allowed to disperse uniformly on the surface. Then, the membrane was left standing for 8 minutes in a glass container saturated with water vapour. Then, the membrane was quickly washed with water to expel excess surface active agent solution. Subsequently, the membrane was washed with distilled water for 30 minutes for removal of molecules of excess surface active agent remaining within the micropores. The asymmetric membrane obtained by the foregoing treatment was dried under a vacuum. Distilled water was allowed to permeate the dried membrane through the treated surface thereof. Consequently, the membrane was found to be retaining 2.6 mg of water within the micropores thereof. Absolutely no water permeated the membrane through the untreated surface. This fact testifies that this membrane possessed an asymmetrical stratal structure combining one hydrophilic and one hydrophobic layer. When hydrophilicity is conferred upon the same membrane throughout the entire thickness thereof, the membrane is found to be capable of retaining 6.2 mg of water within the micropores thereof. Thus, the depth d to which the membrane of this example was rendered hydrophilic by the aforementioned treatment is estimated to be about 29.5 $\mu$m. Since the speed of permeation was 3.5 $\mu$m/min, the distance of permeation over the period of 8 minutes is found by calculation to be 28 $\mu$m. In consideration of the fact that the micropores are not distributed uniformly within the membrane, it may well be concluded that the two values are in satisfactory agreement.

Now, 15 $\mu$l of an enzyme solution obtained by adding 15% of albumin to an aqueous solution of 1150 units/ml of adenosine deaminase (E. C. 3.5.4.4) was dropped onto the hydrophilic surface of the asymmetrically functional membrane and then left standing under saturated water vapour for 60 minutes to be impregnated with the enzyme solution. The impregnated membrane was wiped with filter paper to remove an excess enzyme solution from the surface. It was then cross-linked with 5% glutalaldehyde for 5 minutes and immersed under a 0.1M glycine solution for one hour to immobilize adenosine deaminase therein. Consequently, there was obtained an asymmetrically functional membrane which combined a function of enzymatic reaction and a function of selective permeation of gas.

The asymmetrically functional membrane thus produced was set up in the place of a gas permeable membrane on a conventional ammonia gas selective electrode. The resultant enzyme electrode was tested for response characteristics relative to adenosine in a 0.1 mol/lit. tris-hydrochloride buffer at pH 8.5 and at 37° C.

Figure 2:
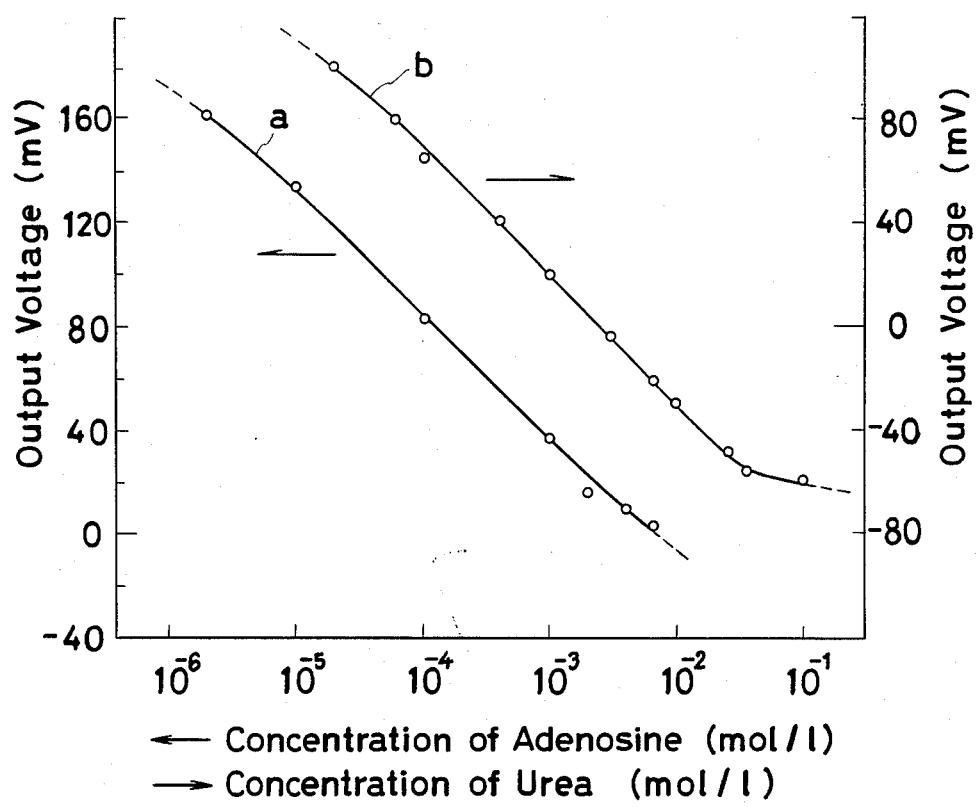
FIG. 2 is a graph showing the relation between the concentration of adenosine and the output voltage (curve a) and the relation between the concentration of urea and the output voltage (curve b) respectively in an enzyme electrode having a functional membrane of this invention as indicated in Examples 1 and 2.

The results of this test, when plotted for the relation between the adenosine concentration ($2 \times 10^{-6}$ to $10^{-2}$ mol/lit.) and the output voltage, described the curve a in the graph of FIG. 2. It is noted from this graph that the output voltage and the adenosine concentration show a good linear relation within the range of adenosine concentration mentioned above. The response time, i.e. the time required for the output voltage to reach a constant value, was 5 minutes for the adenosine concentration of $10^{-5}$ mol/lit., 2 minutes for $10^{-4}$ mol/lit., and 1 minute for $10^{-3}$ mol/lit. respectively. an electrode of a similar nature using two membranes has been reported as by I. Deng (Anal. Chem., 52, 1937, 1980). The response time with this membrane is 7 to 12 minutes for a concentration of not more than $10^{-4}$ mol/lit., 6 to 10 minutes for $10^{-4}$ to $10^{-3}$ mol/lit., and 2 to 4 minutes for $10^{-2}$ mol/lit. Thus, this membrane is noted to respond to adenosine very slowly as compared with the electrode of this invention. This conspicuous contrast demonstrates the advantage of the enzyme electrode using the asymmetrically functional membrane.

The output voltage of the enzyme electrode was stable for at least two weeks at room temperature (as used on 20 test pieces per day).

EXAMPLE 2

On the surface of a square film of sintered porous polytetrafluoroethylene $20 \times 20$ cm$^2$ in area, 150 $\mu$m in thickness, 0.1 $\mu$m in average pore diameter, 1.40 in apparent density, and 35% in void ratio, a 3% aqueous solution of nonionic fluorinated surface active agent (having perfluoroalkyl ethylenoxide adduct as its principal component; made by Asahi Glass and marketed under trademark Surfron S-145) was dropped and allowed to disperse uniformly. The membrane was then subjected to the same treatment of impregnation for 10 minutes as in Example 1. It was subsequently washed with water by following the procedure of Example 1, to produce an asymmetrically functional membrane consisting of one hydrophilic and one hydrophobic layer. The depth to which a hydrophilic texture was consequently formed in the membrane was 100 $\mu$m.

Now, by following the procedure of Example 1, an adenosine diaminase-albumin solution or an aqueous solution containing 150 mg of urease (5 units/mg) and 150 mg of albumin was dispersed on the surface of the membrane and immobilized, to produce an asymmetrically functional membrane combining a function of enzymatic reaction and a function of selective gas permeation. By punching disks 1.5 cm in diameter out of the asymmetrically functional membrane, there were obtained a number of enzyme-immobilized membranes suitable for deposition on electrodes.

Each of the two kinds of asymmetrically functional membranes thus obtained was superposed in the place of a gas permeable membrane on an ammonia gas selective electrode and tested in a 0.1 mol/lit. tris-hydrochloride buffer at pH 8.5 and at 37° C. for response characteristics relative to adenosine and in a 0.2 mol/lit. tris-hydrochloride buffer at pH 8.5 and at 25° C. for response characteristics relative to urea.

The results of this test were similar to those of Example 1 with respect to adenosine. The results obtained with respect to urea showed a good linear relation within the range of concentration of $2 \times 10^{-5}$ to $3 \times 10^{-2}$ mol/lit. as indicated by the curve b in FIG. 2. The response time fell in the range of 2 to 5 minutes and the output was stable for at least two weeks.

EXAMPLE 3

By following the procedure of Example 1, a circular membrane of expanded porous polytetrafluoroethylene 1.5 cm in diameter, 70 $\mu$m in thickness, 0.65 $\mu$m in average pore diameter, 0.528 in apparent density, and 75.6% in void ratio was treated with a 0.8% aqueous solution of perfluoroalkyl betaine (S-131) to produce an asymmetrically functional membrane. This membrane was immersed in an enzyme solution obtained by adding 200 mg of oxalate decarboxylase (0.5 unit/mg) to 1 ml of an aqueous solution containing 100 mg of albumin to have the enzyme immobilized in the membrane. The resultant enzyme-immobilized membrane was superposed in the place of a gas permeable membrane on a carbon dioxide gas selective electrode and tested in a citrate-sodium phosphate buffer of pH 3.5 for response characteristics relative to oxalic acid. The results of the test showed a good linear relation between the output voltage and the oxalic acid concentration within the range of oxalic acid concentration of $3 \times 10^{-5}$ to $5 \times 10^{-2}$ mol/lit. The response time fell in the range of 3 to 12 minutes and the output was stable for at least one week.

EXAMPLE 4

One side of a circular membrane of expanded porous polytetrafluoroethylene 1.5 cm in diameter, 70 $\mu$m in thickness, 1 $\mu$m in average pore diameter, 0.45 in apparent density, and 79% in void ratio was treated for one minute with 0.7% aqueous solution of Surfron S-145 (perfluoroalkyl ethylene oxide adduct) made by Asahi Glass. Thereafter, the treated membrane was washed with water by following the procedure of Example 1, to produce an asymmetrically functional membrane consisting of one hydrophilic and one hydrophobic layer. In this case, the depth to which a hydrophilic texture was formed consequently in the membrane was 40 $\mu$m.

Subsequently, adenosine deaminate was immobilized in the membrane in the same way as in Example 1. The enzyme-immobilized membrane was superposed on an electrode and tested for response characteristics relative to adenosine. The results of the test were similar to those obtained in Example 1. The speed of response was improved by about 20%.

EXAMPLE 5

One side of a circular membrane of sintered porous polytetrafluoroethylene 1.5 cm in diameter, 120 $\mu$m in thickness, 0.1 $\mu$m in average pore diameter, 1.4 in apparent density, and 35% in void ratio was treated for three minutes with a 3% aqueous solution of Surfron S-113 (perfluorocarbonate) made by Asahi Glass, to produce an asymmetrically functional membrane consisting of one hydrophilic (80 $\mu$m in depth) and one hydrophobic layer.

Then, by following the procedure of Example 1, 10 $\mu$l of an aqueous solution containing 5 mg of glucose oxidase (134 units/mg) and 5 mg of albumin was dropped onto the membrane to have the enzyme immobilized in the porous membrane matrix. The asymmetrically functional membrane thus obtained and combining a function of enzymatic reaction and a function of selective permeation of gas was superposed on an enzyme electrode and tested in a 50 mM phosphate buffer of pH 7.0 for response characteristics relative to glucose. The results of test showed a good linear relation between the electrode response and the glucose concentration within the range of glucose concentration of $5\times10^{-6}$ to $2\times10^{-3}$M. The response time fell in the range of 20 to 120 seconds. The output was stable for at least one month.

EXAMPLE 6

The same membrane as used in Example 5 was similarly treated for five minutes with a 6% aqueous solution of Surfron S-121 (perfluoroalkyl trimethyl ammonium salt) made by Asahi Glass, to produce an asymmetrically functional membrane containing a hydrophilic texture to a depth of about 90 µm. Now, by following the procedure of Example 5, glucose oxidase was immobilized in the membrane to produce an asymmetrically functional membrane combining a function of enzymatic reaction and a function of selective permeation of gas. This membrane showed the same response as obtained in Example 5.

What is claimed is:

1. A porous asymmetrical polytetrafluoroethylene membrane having an enzyme immobilized therein, said membrane having a thickness of 10 µm to 200 µm and an average pore diameter of 0.01 µm to 10 µm, and composed of a hydrophilic portion of a depth in the range of 30% to 80% of the thickness of the membrane, said hydrophilic portion being formed by contacting a solution of a perfluoroalkyl surface-active agent with one side of said membrane for a time sufficient for said surface-active agent to penetrate said depth of said membrane, and a hydrophobic portion which has a function of selective gas permeation forming the remainder of the membrane thickness, said pores of said hydrophilic portion containing an immobilized enzyme which provides said membrane with a function of enzymatic activity.

2. the membrane of claim 1, wherein said membrane has a thickness of from 200 µm to 50 µm.

3. The membrane of claim 1, wherein said average pore diameter is 0.01 µm to 1 µm.

4. the membrane of claim 1, wherein said surface-active agent is selected from the group consisting of perfluoroalkyl sulfonates, perfluoroalkyl carbonates, perfluoroalkyl phosphoric esters, perfluoroalkyl sulfates, perfluoroalkyl trimethylammonium salts, perfluoroalkyl betaines, and perfluoroalkylethylene oxide adducts.

5. The membrane of claim 1, wherein said perfluoroalkyl surface-active agent is a perfluoroalkyl betaine or a perfluoroalkylethylene oxide adduct.

6. The membrane of claim 1, wherein said solution of perfluoroalky surface-active agent comprises an organic solvent selected from the group consisting of ethanol, 2-propanol and dioxane.

7. The membrane of claim 3, wherein the concentration of said organic solvent is not more than 10%.

8. A method for the manufacture of an asymmetrical porous polytetrafluoroethylene membrane having an enzyme immobilized therein, said membrane composed of two portions, one portion containing the enzyme and the other having a function of selective gas permeation, said method comprising the steps of contacting one surface of a porous polytetrafluoroethylene membrane having a thickness of 10 µm to 200 µm and an average pore diameter of 0.01 µm to 10 µm, with a solution of a perfluoroalkyl surface-active agent having a known speed of permeation into the membrane to thereby impregnate the membrane with the surface-active agent to a depth in the range of 30% to 80% of the thickness of the membrane, thereby making said membrane hydrophilic within said thickness, and leaving the remaining thickness of the membrane free of the surface-active agent to form a hydrophobic portion not impregnated with the surface-active agent, thereafter contacting the hydrophilic portion with an enzyme, whereby said enzyme penetrates said hydrophilic portion of said membrane, and immobilizing said enzyme in said hydrophilic portion of said membrane.

9. The method of claim 8, wherein said contacting is conducted for a time of from 5–20 minutes.

* * * * *